(12) United States Patent
Receveur et al.

(10) Patent No.: US 7,388,459 B2
(45) Date of Patent: Jun. 17, 2008

(54) MEMS SWITCHING CIRCUIT AND METHOD FOR AN IMPLANTABLE MEDICAL DEVICE

(75) Inventors: Rogier Receveur, Maastricht (NL); Cornel Marxer, Neucahtel (CH)

(73) Assignee: Medtronic, Inc., Minneapolis, MN (US)

( * ) Notice: Subject to any disclaimer, the term of this patent is extended or adjusted under 35 U.S.C. 154(b) by 623 days.

(21) Appl. No.: 10/973,117

(22) Filed: Oct. 26, 2004

(65) Prior Publication Data

US 2005/0115811 A1    Jun. 2, 2005

Related U.S. Application Data

(60) Provisional application No. 60/565,015, filed on Apr. 23, 2004, provisional application No. 60/515,042, filed on Oct. 28, 2003.

(51) Int. Cl.
*H01H 51/22* (2006.01)
(52) U.S. Cl. ......................................................... 335/78
(58) Field of Classification Search ................ 257/741, 257/E23.141; 310/307; 335/78
See application file for complete search history.

(56) References Cited

U.S. PATENT DOCUMENTS

| | | | |
|---|---|---|---|
| 4,316,472 A | 2/1982 | Mirowski et al. ........ | 128/419 D |
| 4,375,817 A | 3/1983 | Engle et al. ............. | 128/419 D |
| 4,378,459 A | 3/1983 | Hardman et al. ........... | 556/439 |
| 4,384,585 A | 5/1983 | Zipes ...................... | 128/419 D |
| 4,476,868 A | 10/1984 | Thompson ............. | 128/419 PG |
| 4,566,063 A | 1/1986 | Zolnowsky et al. ......... | 364/200 |
| 4,577,633 A | 3/1986 | Berkovits et al. ..... | 128/419 PG |
| 4,587,970 A | 5/1986 | Holley et al. ......... | 128/419 PG |
| 4,726,380 A | 2/1988 | Vollmann et al. ..... | 128/419 PG |
| 4,727,877 A | 3/1988 | Kallok .................... | 128/419 D |
| 4,800,883 A | 1/1989 | Winstrom ............... | 128/419 D |
| 4,821,733 A | 4/1989 | Peck ........................... | 128/636 |

(Continued)

FOREIGN PATENT DOCUMENTS

WO    WO 00/74557 A1    12/2000

(Continued)

OTHER PUBLICATIONS

Wang, Y. et al., "A Micromachined RF Microrelay with Electrothermal Actuation," *Sensors and Actuators A*, vol. 103, p. 231-236 (2003).

*Primary Examiner*—Zandra Smith
*Assistant Examiner*—Paul E Patton
(74) *Attorney, Agent, or Firm*—Michael C. Soldner

(57) ABSTRACT

A bistable MEMS switch for use in selectively opening or closing electrical circuits included in an implantable medical device system is provided. The switch includes a central movable beam having a movable contact; a suspension system for supporting the movable beam and generating a contact force; an actuator for displacing the beam upon application of an activation signal, and a fixed contact for interfacing the movable contact when the switch is in a closed state. The switch is fabricated from a $Si/SiO_2/Si$ wafer using photolithography, DRIE and sacrificial oxide etching followed by metalization of electrical contact points with a wear-resistant metal or alloy. An actuation layer may be fabricated from the silicon substrate layer of the wafer and the signal layer may be fabricated from the top silicon layer. The actuation layer and signal layer are thereby electrically decoupled and mechanically coupled by the intervening $SiO_2$ layer.

8 Claims, 13 Drawing Sheets

U.S. PATENT DOCUMENTS

| | | | | |
|---|---|---|---|---|
| 4,830,006 A | 5/1989 | Haluska et al. | ....... | 128/419 PG |
| 4,880,005 A | 11/1989 | Pless et al. | ........... | 128/419 PG |
| 4,949,719 A | 8/1990 | Pless et al. | ............ | 128/419 D |
| 4,953,551 A | 9/1990 | Mehra et al. | ........... | 128/419 D |
| 5,025,346 A | 6/1991 | Tang et al. | ................ | 361/283 |
| 5,097,830 A | 3/1992 | Eikefjord et al. | ....... | 128/419 D |
| 5,099,838 A | 3/1992 | Bardy | .................... | 128/419 D |
| 5,117,824 A | 6/1992 | Keimel et al. | .......... | 128/419 D |
| 5,131,388 A | 7/1992 | Pless et al. | ............ | 128/419 D |
| 5,144,949 A | 9/1992 | Olson | .................. | 128/419 PG |
| 5,158,078 A | 10/1992 | Bennett et al. | ....... | 128/419 PG |
| 5,163,427 A | 11/1992 | Keimel | .................. | 128/419 D |
| 5,188,105 A | 2/1993 | Keimel | .................. | 128/419 D |
| 5,199,428 A | 4/1993 | Obel et al. | ............. | 128/419 C |
| 5,207,218 A | 5/1993 | Carpentier et al. | ... | 128/419 PG |
| 5,269,298 A | 12/1993 | Adams et al. | ......... | 128/419 D |
| 5,312,453 A | 5/1994 | Shelton et al. | ................ | 607/19 |
| 5,314,430 A | 5/1994 | Bardy | ........................... | 607/5 |
| 5,330,507 A | 7/1994 | Schwartz | ..................... | 607/14 |
| 5,331,966 A | 7/1994 | Bennett et al. | ............ | 128/696 |
| 5,354,316 A | 10/1994 | Keimel | ........................ | 607/15 |
| 5,415,043 A | 5/1995 | Zabler et al. | ........... | 73/517 AV |
| 5,545,186 A | 8/1996 | Olson et al. | ................... | 607/14 |
| 5,619,177 A * | 4/1997 | Johnson et al. | ............. | 337/140 |
| 5,662,692 A | 9/1997 | Paspa et al. | .................... | 607/37 |
| 5,690,686 A | 11/1997 | Min et al. | ....................... | 607/5 |
| 5,797,970 A | 8/1998 | Pouvreau | ...................... | 607/9 |
| 5,800,465 A | 9/1998 | Thompson et al. | ........... | 607/9 |
| 5,833,710 A | 11/1998 | Jacobson | ....................... | 607/4 |
| 5,914,553 A | 6/1999 | Adams et al. | ............. | 310/309 |
| 6,020,564 A | 2/2000 | Wang et al. | ................ | 200/181 |
| 6,070,101 A | 5/2000 | Struble et al. | .................. | 607/9 |
| 6,081,748 A | 6/2000 | Struble et al. | .................. | 607/9 |
| 6,114,794 A | 9/2000 | Dhuler et al. | ............... | 310/307 |
| 6,122,545 A | 9/2000 | Struble et al. | .................. | 607/9 |
| 6,137,206 A | 10/2000 | Hill | ............................ | 310/306 |
| 6,148,234 A | 11/2000 | Struble | ........................ | 607/28 |
| 6,153,839 A | 11/2000 | Zavracky et al. | ........... | 200/181 |
| 6,191,671 B1 | 2/2001 | Schlaak et al. | ................ | 335/78 |
| 6,303,885 B1 * | 10/2001 | Hichwa et al. | ............. | 200/181 |
| 6,307,169 B1 | 10/2001 | Sun et al. | .................... | 200/181 |
| 6,388,359 B1 | 5/2002 | Duelli et al. | ................ | 310/309 |
| 6,433,657 B1 | 8/2002 | Chen | .......................... | 333/262 |
| 6,529,093 B2 | 3/2003 | Ma | ............................. | 333/101 |
| 6,531,668 B1 | 3/2003 | Ma | ............................. | 200/181 |
| 6,566,617 B1 | 5/2003 | Suzuki et al. | ............... | 200/181 |
| 6,580,337 B1 | 6/2003 | Valas | ......................... | 333/105 |
| 6,635,837 B2 | 10/2003 | Subramanian et al. | ...... | 200/181 |
| 6,686,820 B1 | 2/2004 | Ma et al. | ..................... | 333/262 |
| 6,734,770 B2 | 5/2004 | Aigner et al. | ................. | 335/78 |
| 6,800,912 B2 | 10/2004 | Ozgur | ........................ | 257/414 |
| 6,894,420 B2 * | 5/2005 | Rodgers | ..................... | 310/309 |
| 2002/0075094 A1 | 6/2002 | Bechtle et al. | ............... | 333/105 |
| 2002/0095187 A1 | 7/2002 | Thompson et al. | ............ | 607/9 |
| 2003/0058069 A1 | 3/2003 | Schwartz et al. | ............. | 335/78 |
| 2003/0093130 A1 | 5/2003 | Stypulkowski | ............... | 607/46 |
| 2003/0117257 A1 | 6/2003 | Cunningham | ............... | 338/200 |
| 2003/0132824 A1 | 7/2003 | Ma | ............................. | 335/78 |
| 2003/0183008 A1 * | 10/2003 | Bang et al. | ............... | 73/514.01 |
| 2004/0008097 A1 | 1/2004 | Ma et al. | ..................... | 333/262 |
| 2004/0050675 A1 | 3/2004 | Feng et al. | ................. | 200/181 |
| 2004/0056740 A1 | 3/2004 | Ma et al. | ..................... | 333/262 |

FOREIGN PATENT DOCUMENTS

| | | |
|---|---|---|
| WO | WO 01/06543 A2 | 1/2001 |
| WO | WO 02/075429 A1 | 9/2002 |
| WO | WO 03/028059 A1 | 4/2003 |
| WO | WO 03/040338 A2 | 5/2003 |
| WO | WO 2004/013898 A2 | 2/2004 |
| WO | WO 2004/096348 A2 | 11/2004 |

\* cited by examiner

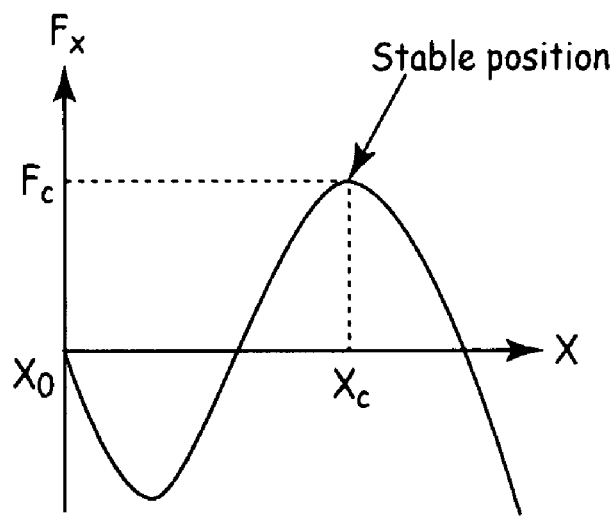
FIG. 6
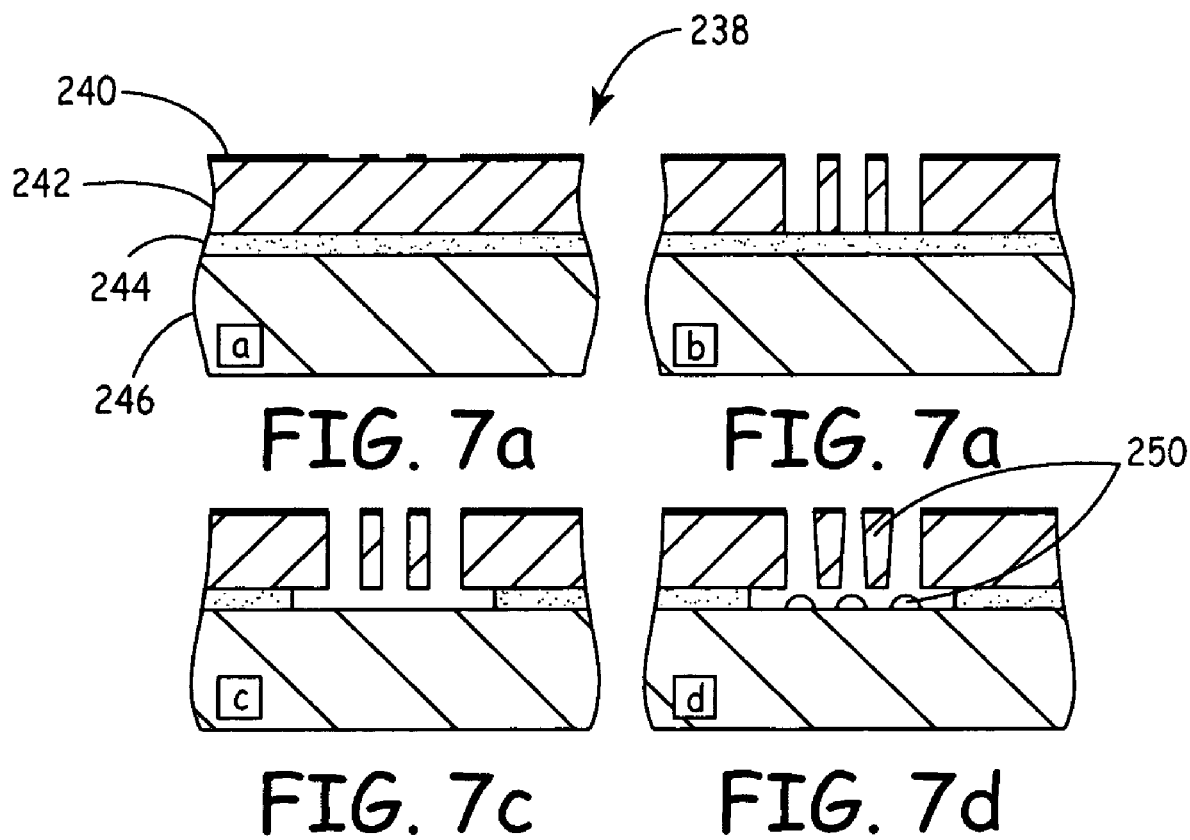
FIG. 7a       FIG. 7a
FIG. 7c       FIG. 7d

TABLE 1 TYPICAL PARAMETER VALUES

| Parameter | Description | Value | Unit |
|---|---|---|---|
| Bi-stable switch | | | |
| l | Overlap of comb finger | 20 | μm |
| w | Width of comb finger | 3 | μm |
| g | Gap between comb fingers | 2 | μm |
| d | Tip-base distance combs | 15 | μm |
| h | Height of combs | 50 | μm |
| $L_h$ | Total arm length of hinges | 500 | μm |
| $l_h$ | Length of hinges | 100 | μm |
| $t_h$ | Thickness of hinges | 3 | μm |
| $t_1$ | Thickness double clamped beam | 10 | μm |
| $L_1$ | Length double clamped beam | 180 | μm |
| $x_0$ | Offset | 8 | μm |
| $x_c$ | Contact position | 12 | μm |
| N | Number of moving fingers | 240 | # |
| Micro-stable switch (all comb actuator parameters identical to bi-stable case) | | | |
| $l_h$ | Length of hinges | 800 | μm |
| $t_h$ | Thickness of hinges | 7 | μm |
| N | Number of moving fingers | 300 | # |

FIG. 18

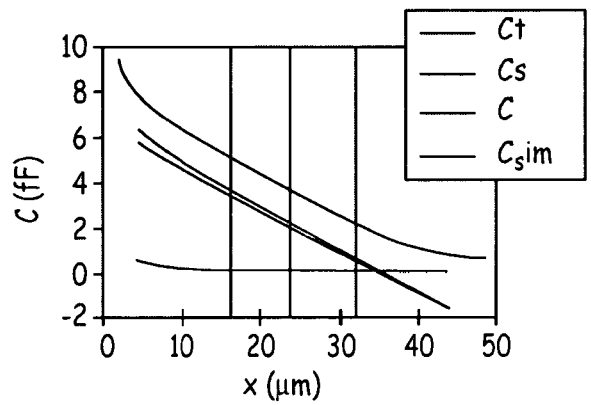

FIG. 20

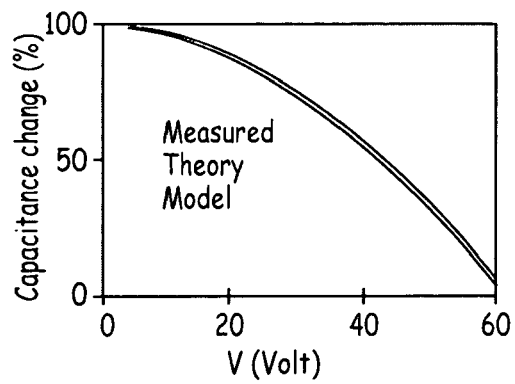

FIG. 21

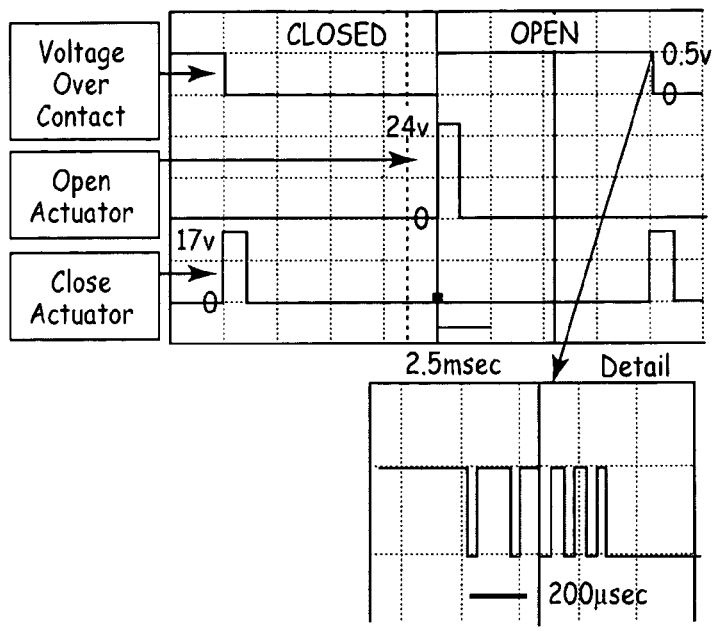
FIG. 22
FIG. 22A
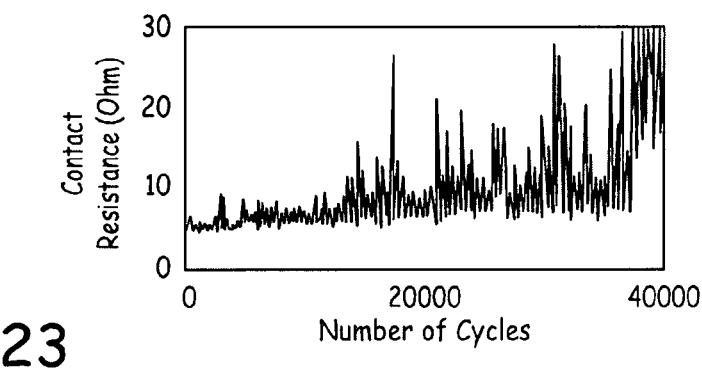
FIG. 23
FIG. 24
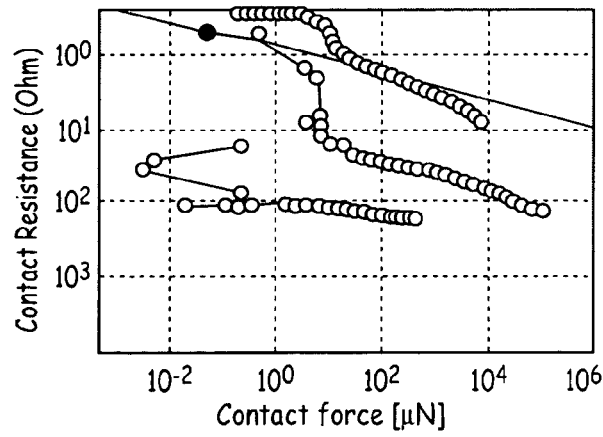
FIG. 26

MEMS SWITCHING CIRCUIT AND METHOD FOR AN IMPLANTABLE MEDICAL DEVICE

RELATED APPLICATION

This application claims priority to and the benefit of U.S. Provisional Application No. 60/515,042 filed Oct. 28, 2003, incorporated herein by reference in its entirety and U.S. Provisional Application No. 60/565,015 filed Apr. 23, 2004, incorporated herein by reference in its entirety.

FIELD OF THE INVENTION

The present invention relates to an improved system and method for performing switching in an implantable medical device; and, more specifically, relates to the use of micro-electrical mechanical systems (MEMs) technology to implement switching circuitry of an implantable medical device.

BACKGROUND OF THE INVENTION

Many implantable medical devices (IMDs) include circuits for delivering electrical stimulation to tissue. For example, implantable pacing, defibrillation, and cardioversion devices are designed to deliver electrical stimulation to the heart via electrodes that are in contact with cardiac tissue. Other types of implantable devices such as neurostimulation systems are known for delivering electrical stimulation to muscle, nerve, or other types of tissue within a patient's body.

IMDs that deliver electrical stimulation generally include output switching networks to selectively couple stimulation energy to cardiac, muscular, or neurologic tissue from batteries and/or capacitors under supervisory control of algorithms or firmware resident in the device. In the prior art, these switches are generally implemented in CMOS technology using CMOS Field Effect Transistors (FETs). These transistors can be readily implemented in silicon devices using three to five-micron, or larger, CMOS technology. However, as the feature size of the CMOS FETs is decreased below three microns, the breakdown voltage of the FETs is also decreased. If the breakdown voltage decreases to a voltage that is at, or near, the voltage that will be applied across a FET, stimulation pulse parasitic leakage will occur, causing ineffective stimulation, increasing battery current drain, and potentially resulting in damage to the integrated circuit.

One proposed mechanism for solving the above-described problem involves implementing all switching circuitry in at least a three-micron technology in a first integrated circuit, while implementing all other circuitry for the IMD in another integrated circuit employing smaller-sized gates. This type of approach is described in U.S. Pat. No. 5,833,710 to Jacobson. This proposed solution adds an additional integrated circuit to the design, increasing system size and cost.

Moreover, this method requires the addition of hybrid circuit interconnects to couple the multiple integrated circuits. These interconnections are costly to manufacture and are prone to failure. Also, interconnections on the hybrid circuit level generally consume more current than interconnections contained within a single integrated circuit.

Another solution to the problem involves employing several FET transistors in series in place of a single FET to implement a switching function. This allows a given voltage drop to be shared by multiple transistors such that the likelihood of circuit damage and/or leakage is decreased. However, this solution has the disadvantage of greatly increasing the amount of silicon area required to implement each switch. Additionally, the design is complicated because the multiple FETs implementing a single switch must be enabled in a predetermined order to prevent the full voltage drop from being experienced by a single FET even for a very brief period, since this could damage the circuit or cause large leakage currents. The implementation of this design approach therefore generally results in the use of a significantly increased silicon die area.

Yet another approach is discussed in U.S. Pat. No. 5,097,830 to Eikefjord, et al. This patent describes an external defibrillator that incorporates transfer relays to deliver the defibrillation pulse to a patient. This design consumes a relatively large amount of space.

While the above discussion focuses on switching networks used within output circuitry of an IMD, those skilled in the art will recognize that other switches in an IMD are associated with problems similar to those discussed above. What is needed, therefore, is an improved switching system and method for use in implementing a switching function within an IMD or associated lead that can be robustly implemented using a substantially smaller die area and/or meet the low power requirements needed to conserve battery energy in an implanted device.

BRIEF SUMMARY OF THE INVENTION

The present invention is directed toward an improved switching system for use with an implantable medical device (IMD) system. The improved switching system utilizes micro-electro-mechanical system (MEMS) switches in place of one or more switches conventionally implemented using transistor networks. According to one aspect of the invention, a bistable MEMS switch is provided including a central movable beam having a contact located on a forward end of the beam; a dual spring suspension system for supporting the movable beam including double clamped beams coupled to the movable beam and suspension members coupled between the double clamped beams and mechanical ground; an actuator for causing the beam to change state positions upon an activation signal, and a fixed contact. In a "closed" position, the movable contact located on the central beam is in electrical contact with the fixed contact to close a circuit within the IMD or an associated lead or adaptor.

In an "open" circuit position, the fixed contact is located a distance, $x_c$, from the movable contact. The switch is fabricated to have a distance $x_c$ between the movable and fixed contacts in the "open" position such that displacement of the central beam a distance of $x_c$ results in a maximum spring force, $F_c$, imposed by the dual spring suspension system to maintain a reliable contact force between the movable and fixed contacts when the switch is closed. A relatively high contact force is achieved using a relatively low actuation voltage or area.

According to another aspect of the present invention, the bistable MEMS switch is fabricated from a Si/SiO$_2$/Si wafer using photolithography with a single mask, deep reactive ion etching and sacrificial oxide etching followed by metalization of electrical contact points. Separate actuation and signal layers may be provided by using the backside, silicon substrate layer of the wafer for fabricating the actuation layer and the top silicon layer for fabricating the signal layer. The actuation layer and signal layer are thereby electrically decoupled and mechanically coupled by the intervening SiO$_2$ layer.

In various implementations of the present invention, lead conductor/electrode selection circuitry included in an IMD or an associated lead or adaptor, IMD output and protection circuitry and/or IMD power control circuitry may include one or more bistable MEMS switches provided by the present invention for achieving necessary switching functions for opening and closing various circuits within the IMD system. According to one embodiment, the invention involves an IMD that is capable of providing electrical stimulation to a patient where the output switches are implemented using the bistable MEMs switch of the present invention. In another embodiment, the invention involves an IMD including a first circuit that is capable of providing electrical stimulation to a patient, and a switching circuit including a bistable MEMs switch that selectively allows the electrical stimulation to be routed to the desired electrode configuration. The first circuit may be a circuit to deliver pacing pulses, a high-voltage output circuit as may be included in a defibrillation system, a neurostimulator output circuit, or another type of electrical stimulation output system.

In a further embodiment the output circuit implemented in the IMD may include a return current path that is selectable using switches implemented using a bistable MEMS switch. In an additional embodiment, the IMD may include a surge protection circuit implemented using a bistable MEMS switch, where a switch or switches may open upon sensing a condition that may damage the implanted device. In yet another embodiment, the invention may include a MEMs switch or switches used to selectively apply power to one or more circuits in an IMD.

According to one aspect of the invention, a method of controlling delivery of electrical stimulation to a body or sensing electrical body signals is provided, including the steps of generating a stimulation signal, and utilizing a MEMs switch to control delivery of that stimulation signal to the body. The MEMs switch state is controlled using electrical signals (or other activation signals) delivered to the actuator. An appropriate combination of bistable MEMS switches may be switched to respective open or closed states such that a desired electrode configuration is selected. Such electrode selection circuitry employing a bistable MEMS switch may be implemented in an IMD or in an associated lead or adaptors.

BRIEF DESCRIPTION OF THE DRAWINGS

FIG. 6 is a plot of the spring force ($F_x$) of suspension members, included in the switch of FIG. 5, as a function of lateral displacement, x, of a movable contact.

FIG. 7 is an illustration of one method for fabricating the bistable MEMS switch of FIG. 5.

FIG. 18 is a table of typical parameter values utilized in a switch according to the present invention.

FIG. 20 is a graphical representation of capacitance displacement.

FIG. 21 is a graphical representation of relative capacitance change.

FIGS. 22 and 22A are schematic diagrams of voltage over contacts and on actuators during operation of a switch according to an embodiment of the present invention.

FIG. 23 is a graphical representation of contact resistance.

FIG. 24 is a schematic illustration of damage in gold coverage at contact spots compared to untouched areas.

FIG. 26 is a graphical representation of contact resistance and contact force.

DETAILED DESCRIPTION OF THE PREFERRED EMBODIMENTS

Figure 1:
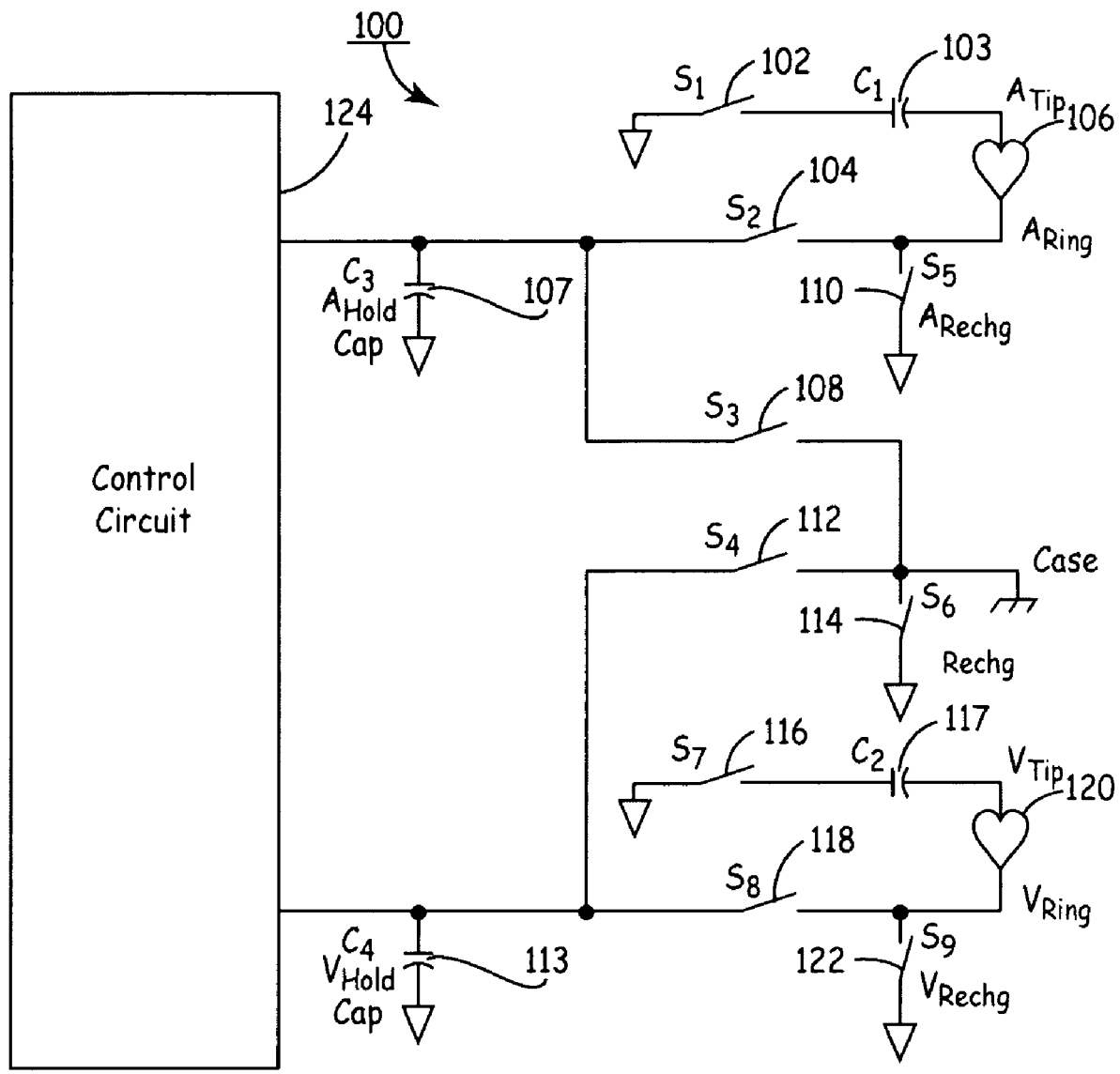
FIG. 1 is a block diagram illustrating a typical switching network used in implantable medical devices.

FIG. 1 is a block diagram illustrating a typical prior art switching network 100 used in implantable medical devices. Switches S1 102 and S2 104 provide atrial bipolar pacing pulses to the atrial chamber 106 of the heart. The stimulation pulse is coupled to the heart via a coupling capacitor 103 from an atrial holding capacitor 107. Similar switches S7 116 and S8 118 provide ventricular bipolar pacing pulses to the ventricular chamber 120 of the heart. These ventricular stimulation pulses are delivered from ventricular holding capacitor 113 via coupling capacitor 117.

Control circuit 124 controls the closure of all switches as well as the voltage levels on holding capacitors 107 and 113. Switches 110 and 122 are closed after the atrial or ventricular stimulation pulses, respectively, have been delivered to allow for the discharge of residual charge residing on capacitors 103 and 117, as well as any charge accumulated at the electrode-tissue interface. Switches 108 and 112 allow unipolar pacing of the atrial and/or ventricular chamber of the heart. Switch 114 allows discharge of capacitors 103 and 117 when pacing in the unipolar mode.

Figure 2:
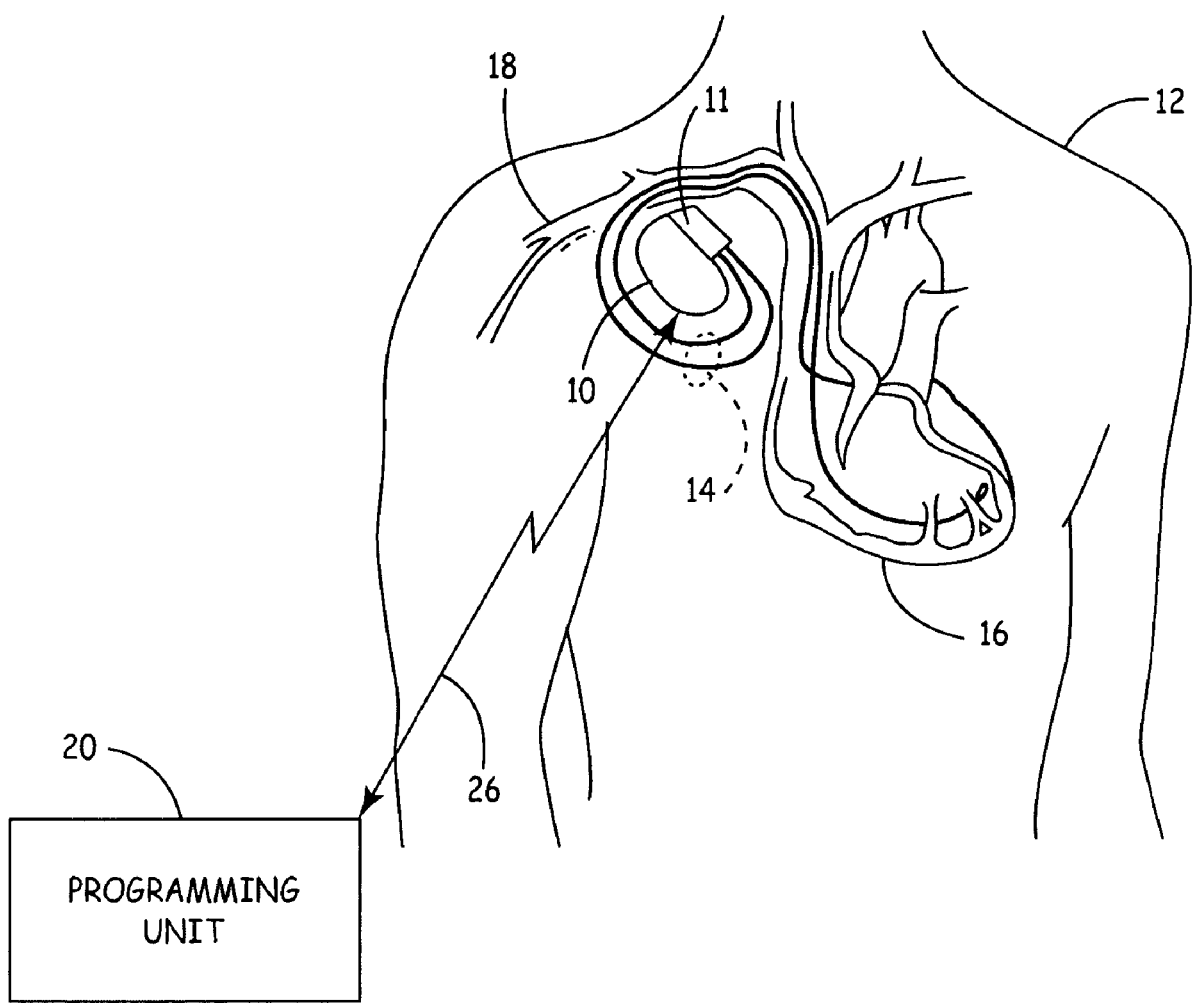
FIG. 2 is a block diagram of an implantable medical device (IMD) that may be adapted to employ the MEMS switches in accordance with the present invention.

FIG. 2 is a block diagram of an implantable medical device (IMD) that may be adapted to employ the switching system of the present invention. Exemplary IMD 10 is shown as a pacemaker implanted in a patient 12. In accordance with conventional practice in the art, pacemaker 10 is housed within a hermetically sealed, biologically inert outer casing, which may itself be conductive so as to serve as an indifferent electrode in a pacing/sensing circuit. One or more pacemaker leads 14 are electrically coupled to IMD 10 in a conventional manner and extend into the patient's heart 16 via a vein 18. Disposed generally near the distal end of leads 14 are one or more exposed conductive electrodes for receiving electrical cardiac signals and/or for delivering electrical pacing stimuli to heart 16. As will be appreciated by those of ordinary skill in the art, the electrodes of leads 14 may be positioned in the atrium and/or ventricle of heart 16. An external programmer 20 is provided for non-invasive communication with IMD 10 via uplink and downlink communication channel 26.

Figure 3:
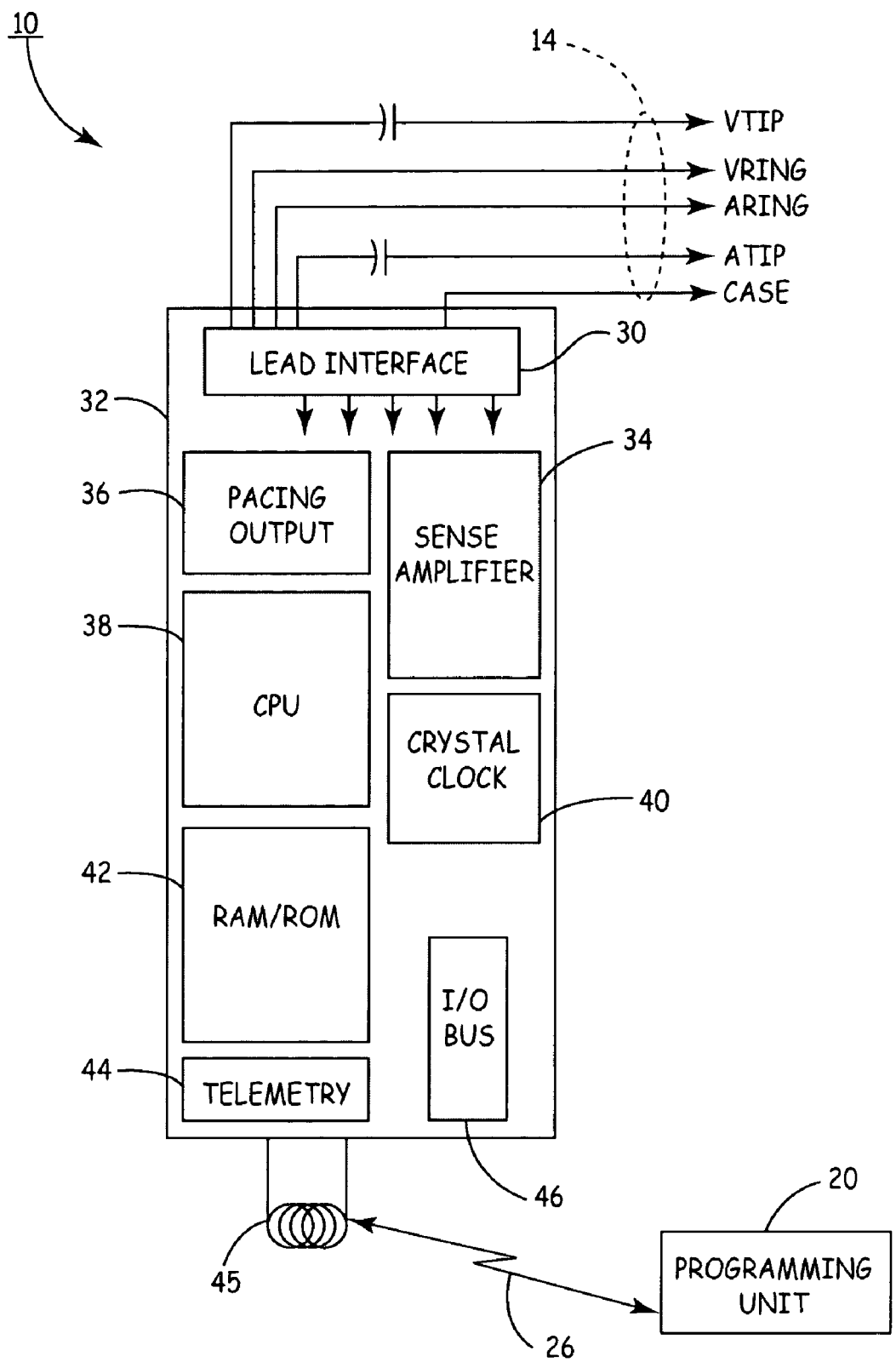
FIG. 3 is a block diagram of electronic circuitry that may be utilized within an implantable medical device such as a pacemaker in accordance with the presently disclosed invention.

FIG. 3 is a block diagram of electronic circuitry that may be utilized within an implantable medical device such as a pacemaker in accordance with the presently disclosed invention. Pacemaker 10 comprises a stimulation control circuit 32 for controlling pacing and sensing functions. Stimulation control circuit 32 may be of conventional design such as disclosed in U.S. Pat. No. 5,052,388 issued to Sivula et al. For example, this circuit may include sense amplifier circuitry 34, stimulating pulse output circuitry 36, a crystal clock 40, a random-access and/or read-only memory (RAM/ROM) unit 42, an I/O Bus 46, and a central processing unit (CPU) 38, all of which are well-known in the art. A communication circuit such as telemetry system 44 may be provided to allow the device to communicate with external programmer 20 via antenna 45 and communication channel 26.

Pacemaker 10 may be coupled to one or more leads 14 that extend transvenously into the patient's heart 16 or associated vascular system. These leads may be connected to the internal circuitry of pacemaker 10 via a standard or nonstandard connector block assembly 11, as shown in FIG. 2. The lead conductors may be electrically coupled with the internal electrical components of pacemaker 10 via a lead interface circuit 30. This interface circuit may be designed to function as a switch to selectively and dynamically establish necessary connections between the circuitry of pacemaker 10 and the various conductors of leads 14, including atrial tip and ring (ATIP and ARING) electrode conductors, and ventricular tip and ring (VTIP and VRING) electrode conductors. The specific connections between leads 14 and the various components of pacemaker 10 are not shown in FIG. 3. However, it will be clear to those of ordinary skill in the art that leads 14 will necessarily be coupled, either directly or indirectly, to sense amplifier circuitry 34 and stimulating pacing output circuit 36.

As previously noted, stimulation control circuit 32 includes central processing unit (CPU) 38 which may be an off-the-shelf programmable microprocessor, a microcontroller, or a custom integrated circuit. CPU 38 executes programmed instructions stored in RAM/ROM unit 42 to control the timed operation of pacing output circuit 36 and sense amplifier circuit 34. Pacing output circuit 36, which generates cardiac stimuli signals, may be of the type disclosed in U.S. Pat. No. 4,476,868 to Thompson incorporated herein by reference in its entirety. Alternatively, any other type of pacing output circuit known in the art may be adapted within the system.

Sense amplifier circuit 34 receives electrical cardiac signals from leads 14. These signals are processed to detect the occurrence of specific cardiac electrical events, including atrial contractions (P-waves) and ventricular contractions (R-waves). Sense amplifier circuit 34 then provides event-indication signals to CPU 38 for use in controlling the synchronous stimulating operations of pacemaker 10 in accordance with common practice in the art. In addition, these event-indication signals may be stored as diagnostic data in RAM/ROM 42 and subsequently communicated via uplink transmission 26 to an external programmer 20.

Control circuit 32 further includes crystal oscillator circuit 40 to provide clock signals for control circuit 32. Other components and subsystems may be provided within the scope of the current invention, including activity sensors and/or any other type of subsystem known for use within an IMD. The various components are powered by a power source such as a battery (not shown) that is contained within the hermetic enclosure of pacemaker 10 in accordance with common practice in the art.

According to one embodiment of the invention, MEMs switches may be utilized in pacing output circuits as discussed above. Specifically, any or all of the switches shown in FIG. 1 may be replaced with MEMs switches. These switches may also be used to implement protection circuits that may be employed instead of Zener diodes to protect sensing circuitry against high-voltage surges.

Through use of MEMs switches, the output system is more reliable, less costly, and results in a much smaller integrated circuit die area so that the overall volume of the IMD may be reduced. The use of MEMs switches may allow the use of smaller geometry integrated circuits for the remaining IMD circuitry. Furthermore, because the MEMs switches can be implemented in a small area, many switches can be incorporated into a single device. For example, a multisite 3- and 4-chamber pacemaker may be implemented easily on a single die. Exemplary devices are described in U.S. Pat. Nos. 6,070,101, 6,081,748, 6,122,545, and 6,148,234 and U.S. Publication No. US2003/0093130A1 incorporated herein by reference in their entireties.

Figure 4:
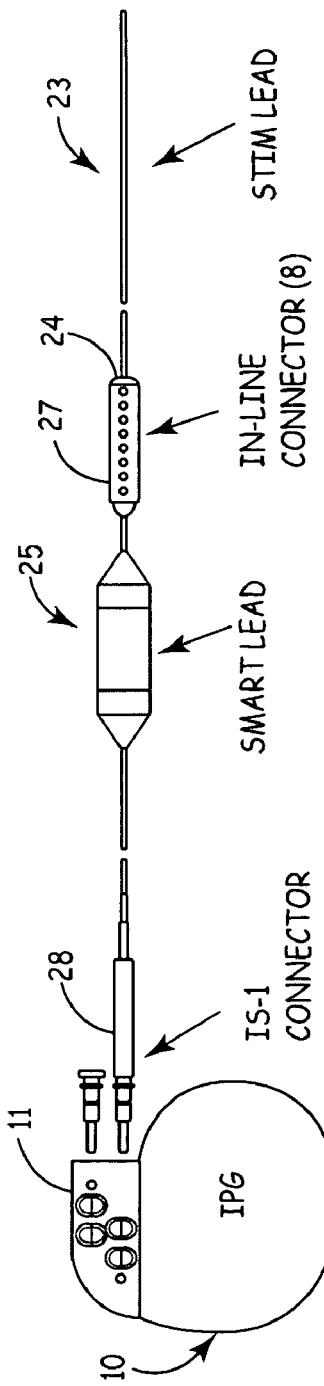
FIG. 4 is an illustration of an implantable medical device coupled to a medical lead via an intermediate adaptor containing switching circuitry for selectively coupling conductors carried by the medical lead to the implantable medical device.

FIG. 4 is an illustration of an implantable medical device coupled to a medical lead via an intermediate adaptor containing switching circuitry for selectively coupling conductors carried by the medical lead to the implantable medical device. The implantable medical device 10 includes connector block 11 configured to receive a lead connector assembly, which may be an IS-1 connector assembly known for use with cardiac pacemakers. In some cardiac or neuromuscular stimulation applications, it is desirable to deploy a multi-polar lead to a stimulation site such that stimulation electrodes may be selected from the multiple electrodes available on the multi-polar lead based on an optimal stimulation response. Furthermore, it may be desirable to select the polarity of each electrode selected for a particular stimulation or sensing configuration.

As such, stimulation lead 23 may be provided as a multipolar lead having an in-line connector assembly 24 provided with multiple connector terminals which are each coupled to a respective conductor carried by stimulation lead 23. An adaptor 25 may be used to couple the multipolar lead to the standard connector block 11 of IMD 10. Adaptor 25 is provided with a multipolar in-line connector port 27 for receiving the multipolar connector assembly 24 of lead 23. Adaptor 25 is further provided with a connector assembly 28 adapted to fit a connection port included in connector block 11.

Adaptor 25 includes switching circuitry (not shown) for selectively coupling terminals located within inline connector port 27 to connectors located on connector assembly 28. For example if connector assembly 28 is provided as a bipolar connector assembly having a pin connector and a ring connector, switches included within adaptor 25 may be used to selectively connect two of the multiple connection terminals within inline connector port 27 to thereby couple two conductors carried by lead 23 to IMD 10. Adaptor 25 can be referred to as a "smart lead" in that adaptor 25 allows selective connection between preferred conductors and respective electrodes of a multipolar lead and connector terminals within IMD connector block 11. Furthermore, switching circuitry included in adaptor 25 may be used to select the polarity (anode, cathode or neutral) of a particular electrode by closing a circuit between the electrode and the desired terminal within conductor block 11.

Adaptor 25 may further include electronics for communicating with IMD 10 and controlling switch state changes, a power supply for providing the power needed to actuate the switches, and feedthroughs for accommodating the in-line connector and connector assembly, all of which may be encased within the adaptor body. An implantable programmable lead adaptor is generally disclosed in commonly-assigned U.S. patent application Ser. No. 10/425,527, filed Apr. 29, 2003 hereby incorporated herein by reference in its entirety.

Preferably, switches included in adaptor 25 require low operating voltage and power consumption so as to minimize the drain on the IMD battery or a separate power source included in adaptor 25, which is preferably of minimal size so as to maintain an overall small size of adaptor 25. Furthermore, switches included in adaptor 25 must provide reliable conductivity by maintaining stable contact and a low resistance when in a closed position. Switches included in adaptor 25 may be provided as bistable MEMS switches according to the present invention.

Figure 5:
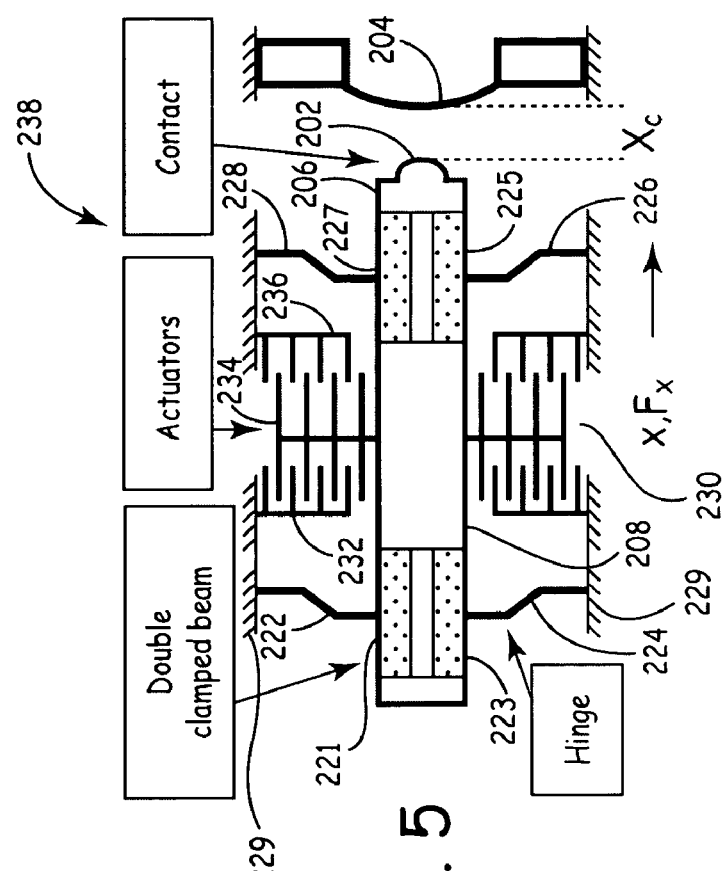
FIG. 5 is a schematic diagram of a bi-stable MEMS DC switch according to the present invention, which may be implemented in any of the switching circuitry described above.

FIG. 5 is a schematic diagram of a bi-stable MEMS DC switch according to the present invention, which may be implemented in any of the switching circuitry described above. Switch 200 is a laterally moving switch designed to meet the stringent power consumption, size, reliability, and contact resistance requirements imposed by chronic, implantable device and lead applications. Switch 200 includes a movable contact 202 and a fixed contact 204. Movable contact 202 is located on a forward end 206 of a movable central beam 208. Central beam 208 is preferably mounted in a dual spring suspension system to allow lateral movement of beam 208 to thereby translate movable contact 202 between two positions, an "open" position and a "closed" position, in a bistable manner.

In the embodiment shown, beam 208 is a centrally mounted using a dual spring suspension system including double-clamped beams 221, 223, 225 and 227 and suspension members 222, 224, 226, and 228. Suspension members 222, 224, 226 and 228 may be provided, for example, as mechanical hinges or springs. Suspension members 222, 224, 226 and 228 are each coupled between a mechanical ground 229 and respective double clamped beams 221, 223, 225, and 227. Double-clamped beams 221, 223, 225, and 227 are each coupled at both ends to central moving beam 208. Suspension members 222, 224, 226 and 228 and double-clamped beams 221, 223, 225, and 227 collectively produce the contact force needed to maintain reliable electrical contact between fixed and movable contacts 202 and 204 as will be further described below.

Lateral movement of beam 208 and movable contact 202 is achieved by actuator 230. Actuator 230 is preferably provided as an electrically-activated actuator such as an electrostatic comb actuator having two interdigitating electrostatic arrays or an electrostatic parallel plate actuator. In the embodiment shown in FIG. 5, two lateral fixed actuator members 232 and 236 will interact with a movable actuator member 234 to cause translation of central beam 208. A "push" electrical voltage pulse may be applied between fixed actuator member 236 and movable actuator member 234 to attract movable actuator member 234 toward fixed member 236, causing beam 208 to move in a forward direction and thereby cause moveable contact 202 to come into contact with fixed contact 204 in a "closed" position. A "pull" electrical pulse may be applied between lateral fixed actuator member 232 and moving member 234 to cause beam 208 to move in an opposite direction and pull movable contact 202 to an "open" position as shown in FIG. 5.

A comb-type electrostatic actuator for use in a MEMS switch is generally described in U.S. Pat. No. 6,388,359, issued to Durelli, incorporated herein by reference in its entirety. It is recognized that other types of actuators may be employed by the present invention, including other electrostatic actuators, electromagnetic actuators, or thermally-activated actuators. Electrostatic actuators are generally preferred, however, because of their fast response time and low power requirements.

In a method for using the bistable MEMS switch provided by the present invention, an activation signal is applied to actuator 230 to cause switch 200 to change state as desired for delivering an electrical stimulation pulse to a patient via a selected electrode or combination of electrodes or for sensing an electrical signal via a selected electrode or combination of electrodes implanted in the patient's body.

FIG. 6 is a plot of the spring force ($F_x$) of suspension members 222, 224, 226, and 228 and double-clamped beams 221, 223, 225, and 227 as a function of lateral displacement, x, of central beam 208. Switch 200 is fabricated such that fixed contact 204 is positioned at a distance $x_c$ from moveable contact 202 when moveable contact is in the "open" position. When moveable contact 202 is advanced a distance of $x_c$ to the "closed" position by actuator 230, the spring force produced by the dual spring suspension system including suspension members 222, 224, 226, and 228 and double-clamped beams 221, 223, 225, and 227 will be at a maximum, $F_c$, and thereby impose a maximum contact force for a stable electrical contact. At position $x_0$, the spring force is 0.

Movable contact 202 and fixed contact 204 are preferably formed from a nickel-gold alloy designed to minimize contact resistance and mechanical wear.

However, alternative wear-resistant contact metals or alloys may be used, such as ruthenium. The Ni/Au alloy was evaporated onto a silicon substrate during fabrication of switch 200 using deep reactive ion etching (DRIE) and sacrificial oxide etching in a silicon-on-insulator (SOI) process.

FIG. 7 is an illustration of one method for fabricating switch 200 according to the present invention. In a first step (a), photolithography is performed on a wafer 238 including a silicon layer 242, a silicon oxide layer 244, and a silicon substrate 246. Standard photolithography techniques are used to remove areas of a photoresist layer 240 in a desired pattern using a mask.

In a second step (b), deep reactive ion etching (DRIE) is performed to remove the silicone layer 242 in the areas exposed during step (a), in a deep profile with approximately vertical side walls. The DRIE step may be adapted such that the vertical side walls shown in FIG. 7 are angled rather than vertical such that the profile of the resulting opening is narrower at the top surface of Si layer 242 and wider at the bottom. In this way, a smaller area of contact between fixed and movable contacts may be formed along angled side walls compared to the relatively larger, flat area of contact formed by vertical side walls.

In step (c), sacrificial oxide etching is performed to remove areas of the silicon oxide layer 244 to expose the silicon substrate layer 246. Thus movable structures are created which are decoupled from the $SiO_2$ layer 242 and underlying Si substrate 246. These movable structures are supported via a suspension system coupled to a mechanical ground as described previously, not shown in FIG. 7.

In a fourth metalization step (d), Ni/Au alloy 250 is evaporated onto the side walls of the top silicon layer 242 thereby forming contact areas. This evaporation step is performed at an angle such that the side walls of the deep profile opening become metalized. Some extraneous metalization of the top surface of Si substrate layer 246 will also occur and care should be taken that this metalization does not contact the upper Si layer 242.

Figure 8:
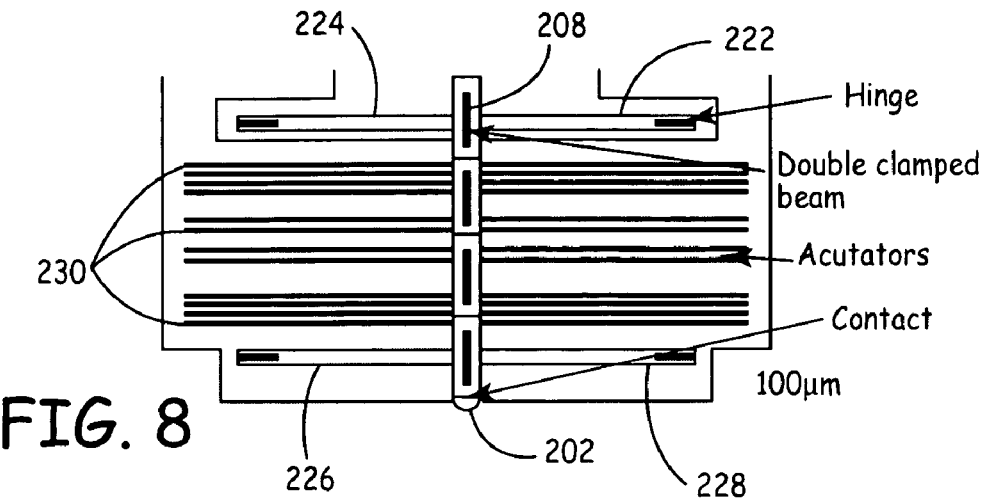
FIG. 8 is a SEM image of a bistable MEMS switch fabricated according to the methods of the present invention.

FIG. 8 is a SEM image of a bistable MEMS switch fabricated according to the methods of the present invention. The overall size of the structure is approximately 1.5 mm×1.5 mm. The electrostatic force per unit area is maximized by choosing the optimum thickness for the top silicon layer 242 (FIG. 7).

Figures 9A, 9B:
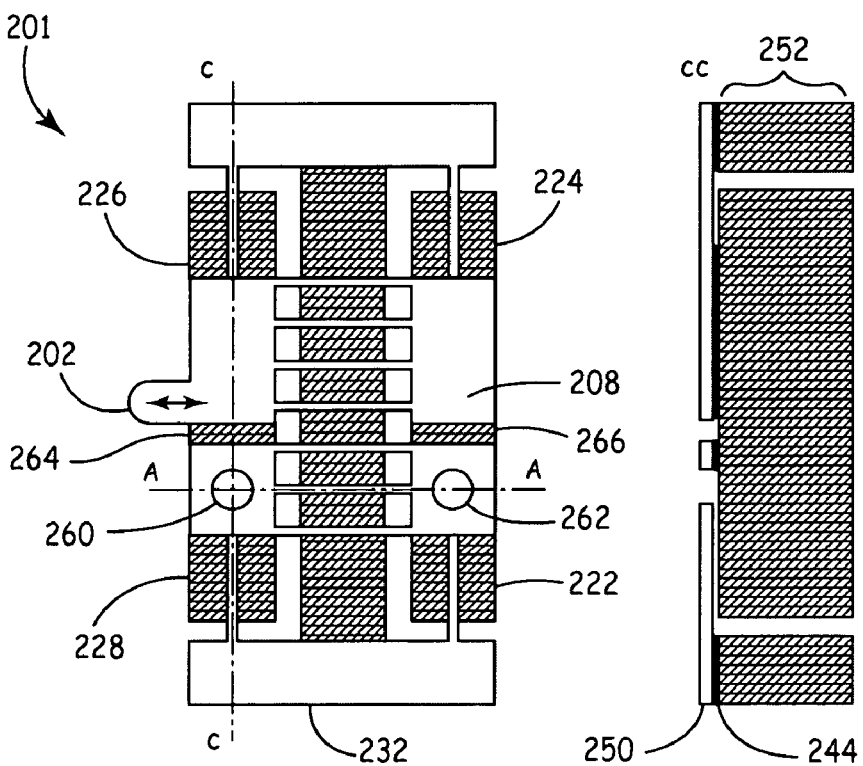
FIG. 9A is a top view of a schematic diagram of an intermediate structure that may be used in fabricating a bistable MEMS switch according to the present invention
FIG. 9B and FIG. 9C are sectional views of the structure shown in FIG. 9A.
Figure 9C:
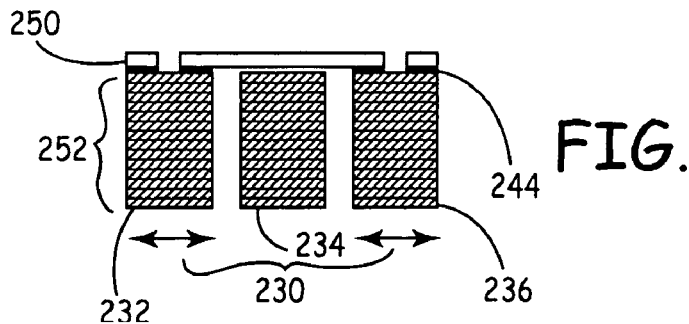

FIG. 9A is a top view of a schematic diagram of an intermediate structure 201 that may be used in fabricating a bistable MEMS switch according to the present invention with sectional views of the structure 201 provided in FIG. 9B and FIG. 9C. In one embodiment, movable beam 208 having movable contact 202, a dual-spring suspension system including suspension members 222, 224, 226, and 228, and fixed contact 204 are included in a signal layer 250 fabricated from the top layer of silicon 242 of a Si/SiO$_2$/Si wafer 238 (FIG. 7). Actuator 230 is fabricated from the silicon substrate layer 246 (FIG. 7) to form an actuator layer 252 using photolithography and DRIE on the backside of the silicon substrate layer 246. The actuator layer 252 and the signal layer 250 are thereby electrically uncoupled. Actuator layer 252 and signal layer 250, however, remain mechanically coupled via silicon oxide layer 244.

In the embodiment shown in FIG. 9A through 9C, actuator 230 includes a central fixed portion 234 and lateral movable portions 232 and 236. By applying a voltage pulse across movable portion 232 and fixed portion 234, actuation of the central beam 208 and movable contact 202 in a direction to close the switch is achieved; by applying a voltage pulse across movable portion 236 and fixed portion 234, actuation of central beam 208 and movable contact 202 in an opposite direction to open the switch is achieved.

Electrical connectivity to the actuation layer for delivering activation signals may be achieved via an electrically conductive suspension member and selective metalization through openings made in the signal layer 250. For example, electrical connection needed for delivering a voltage pulse to laterally moving actuation member 232 may be achieved via electrically conductive suspension member 228 and selective metalization through opening 260 which is made by etching through the top Si layer 242 and SiO$_2$ layer 244. Likewise, electrical connection to laterally moving actuation member 236 may be achieved through electrically conductive suspension member 222 and selective metalization through opening 262. Electrical connection could alternatively be made by selective metalization through openings made by etching through the top Si layer 242 and SiO$_2$ layer 244 at alternate locations than those shown in FIG. 9A and such electrical connection may or may not include suspension members 222, 224, 226 and/or 228.

Thus electrical coupling to the movable components of an actuation layer is achieved through the signal layer. In order to maintain electrical decoupling of the central beam 208 and movable contact 202 from the actuation layer 252 when suspension members 222 and 228 are used to achieve electrical connectivity to the actuation layer 252, the signal layer may be electrically split in two by creating openings 264 and 266 in Si layer 242. The signal layer 250 remains mechanically joined via the SiO$_2$ layer 244 and the actuation layer 252.

The structure 201 is an intermediate structure obtained during fabrication of a bistable MEMS switch having electrically decoupled actuation and signal layers. It is recognized that modifications and variations of structure 201 may be made by one having skill in the art and the benefit of the teachings provided herein in fabricating a bistable MEMS switch without departing from the scope of the present invention.

It is desirable to electrically uncouple the actuation and signal layers to prevent interference between them. In prior art, electrical decoupling of signal and actuation layers has been achieved by stacking multiple conductive layers separated by insulating layers on top of a silicon substrate. However, this method requires additional manufacturing steps and increases the overall size of the wafer. By utilizing the silicon substrate on the back side of the wafer for fabricating the actuation layer, the overall size remains smaller and the number of manufacturing steps is less than prior art methods.

By electrically decoupling the actuator and signal levels 252 and 250, respectively, independent optimization of silicon layer thickness 242 and 246 and dimensioning of actuator and signal layer components may be achieved. For example, different layer thicknesses may allow the force required to change states to be optimized such that "bouncing" of the contacts due to underdamping is avoided and bistability is maintained. The actuator layer 252 may be optimized for maximum force per unit area at a minimum actuation voltage. Signal layer 250 may be optimized for optimum contact properties and mechanical spring forces. The separate actuation layer 252 allows a relatively large displacement of beam 208 and moveable contact 202 using a relatively low voltage. Normally a high actuation voltage or a large area are needed to obtain a reliable contact force. The design provided by the present invention allows generation of a reliable contact force with a minimum amount of area or a minimum actuation voltage.

A relatively large contact force can be obtained by optimizing the distance between the fixed contact 204 and movable contact 202 based on the spring force properties of suspension members 222, 224, 226 and 228 and double-clamped beams 221, 223, 225, and 227 and designing the actuator 230 to displace movable contact 202 this optimal distance. The etched contact members 202 and 204 are well-defined and fabricated to have a minimal contact resistance and mechanical wear properties that exceed the expected cycling times needed over the useful life of the implanted medical device.

Figure 10A:
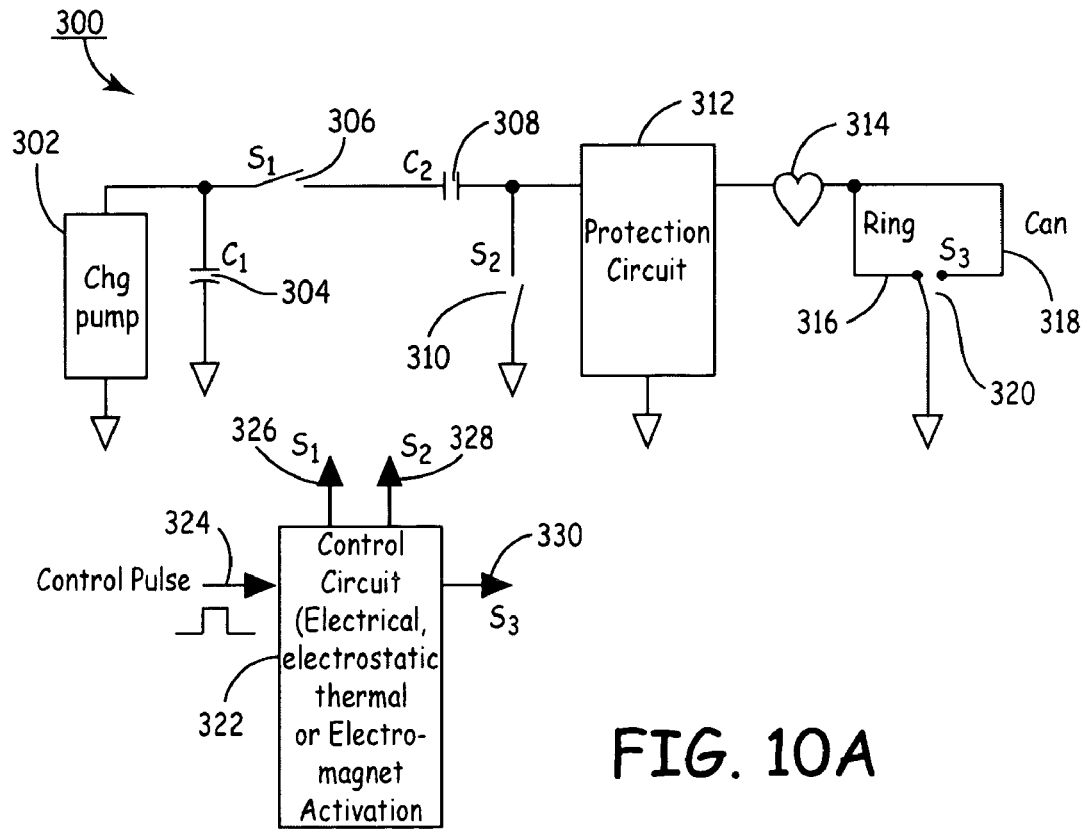
FIG. 10A is a circuit diagram illustrating one embodiment of an output circuit 300 which may utilize the bistable MEMS switch of the present invention.

The bistable MEMS switch of the present invention is not limited to lead-selection switching circuitry applications described above in conjunction with FIGS. 1 and 4. A number of circuits used within IMDs which require switching systems and which may be improved by the use of a MEMS switch are generally described in commonly-assigned U.S. Patent Application Publication No. 2002/0095187 to Thompson et al., incorporated herein by reference in its entirety. FIG. 10A is a circuit diagram illustrating one embodiment of an output circuit 300 which may utilize the bistable MEMS switch of the present invention. This embodiment incorporates a device protection circuit 312. Charge pump 302 and capacitor 304 store a pre-programmed output charge. This output charge may be a high-voltage charge as is used within a cardioversion or defibrillation system, or could be an output charge used in a pacing application. A control pulse 324 is delivered via control circuit 322 and control line 326 to close switch 306. The control circuit may operate based, in part, on physiological signal measurements obtained from the body, including EGM, pressure, temperature, blood flow, or any of the other physiological signal measurements acquired using sensing devices known in the art.

After the switch 306 is closed, the charge stored on capacitor 304 is delivered to the heart 314 via coupling capacitor 308 and protection circuit 312. The return current path is selectably provided by ring 316 or can 318 based on the positioning of switch 320, which may be controlled by control line 330 of control circuit 322. After delivery of the pacing pulse, switch 310 may be closed for 5 to 10 millisecond to discharge the lead/tissue interface polarization voltage, as controlled by control line 328.

Figure 10B:
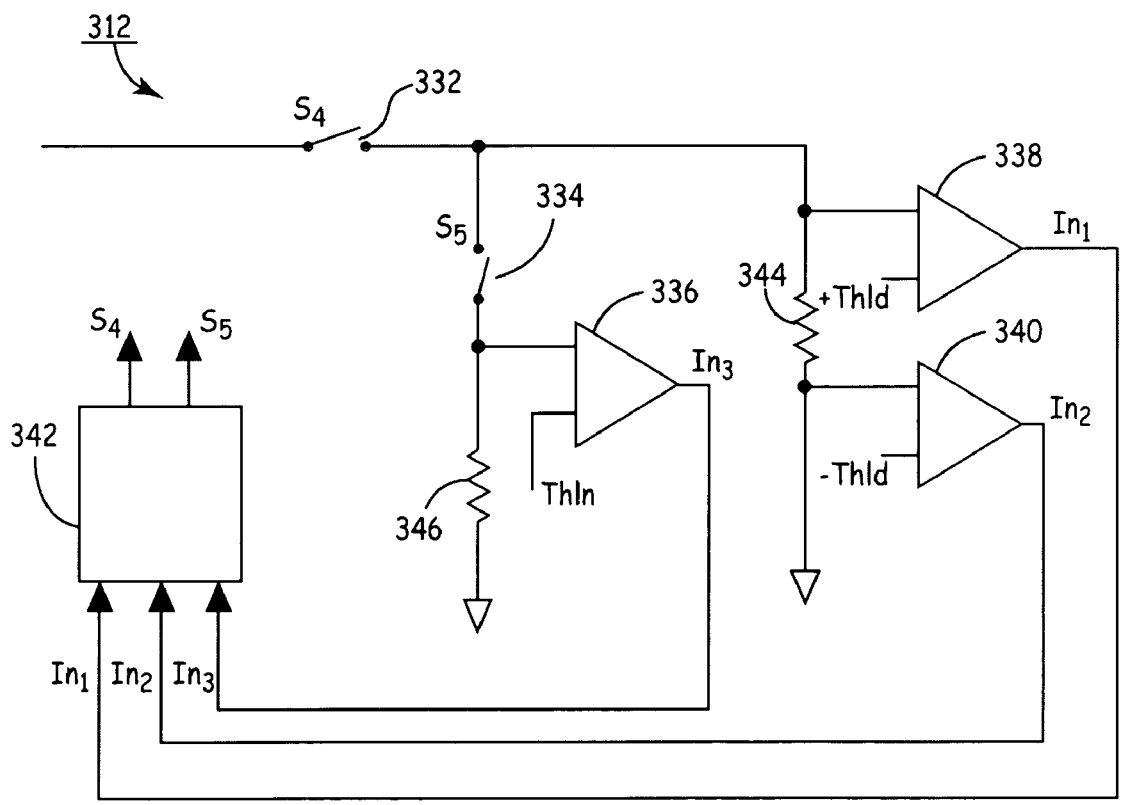
FIG. 10B is a circuit diagram illustrating one embodiment of protection circuitry included in the circuit of FIG. 10A.

FIG. 10B is a circuit diagram illustrating one embodiment of protection circuitry 312. During normal operation, series switch 332 is closed to allow pacing pulses to stimulate the heart 314. During large signal perturbations on the lead system 14, a voltage is applied to positive and negative comparators 338 and 340, respectively. If a large voltage is sensed across the resistor 344, one of the comparators will switch depending upon the polarity of the input signal. Protection control circuit 342 will, in turn, cause switch 332 to open and switch 334 to close providing protection to IMD 10. Current flow through resistor 346 and closed switch 334 will allow comparator 336 to latch the protection control circuit in this mode until the signal is removed.

Any of the switches included in output circuit 300 and protection circuit 312 may be implemented using a bistable MEMS switch according to the present invention or a combination of bistable MEMS switches to achieve the desired switching functions described above.

Figure 11:
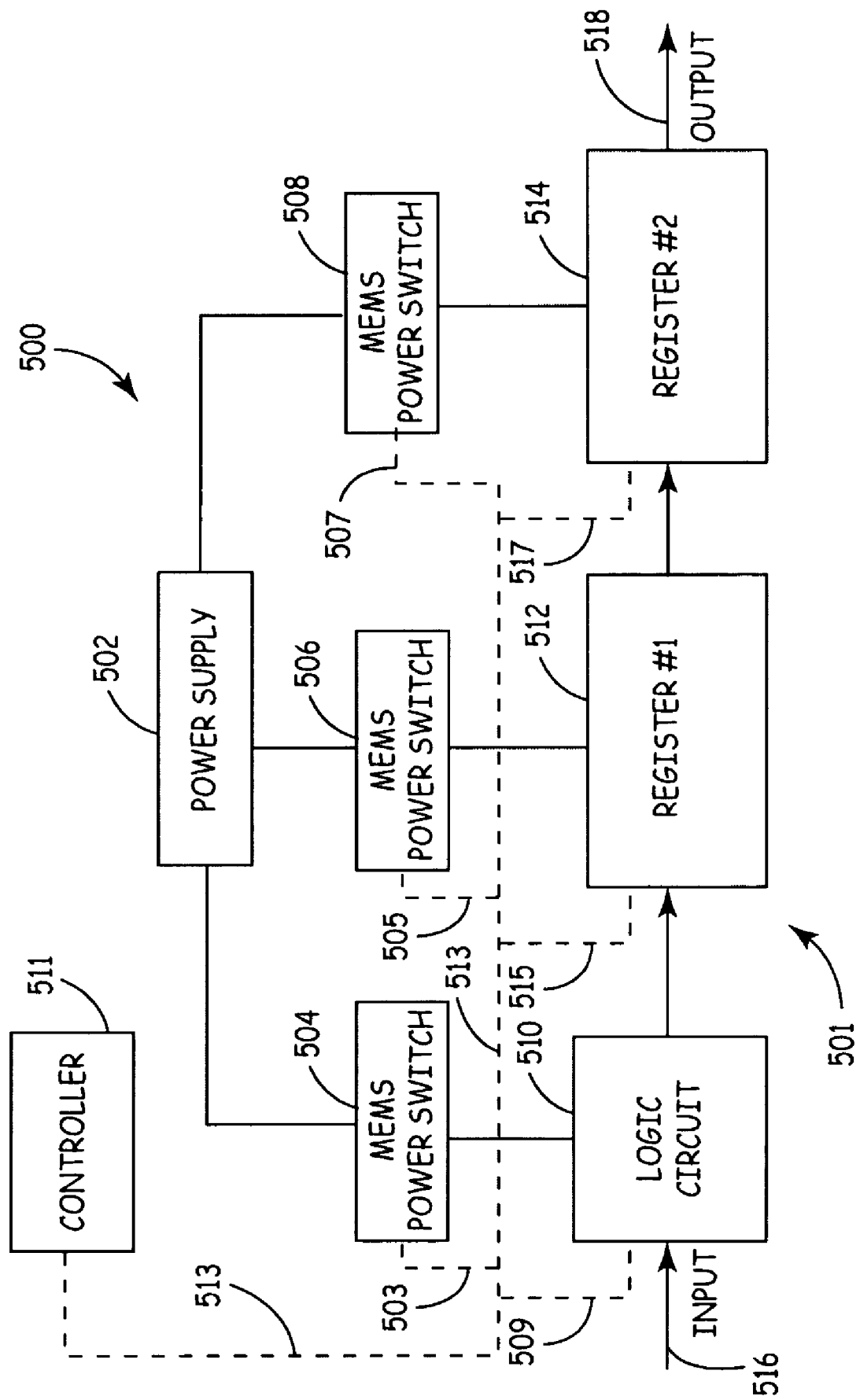
FIG. 11 is a block diagram illustrating a circuit which may implement the MEMS switch provided by the present invention for selectively applying power to one or more circuits in an IMD.

FIG. 11 is a block diagram illustrating a circuit which may implement the MEMS switch provided by the present invention for selectively applying power to one or more circuits in an IMD. A method and apparatus for selectively powering circuits in an IMD using standard CMOS switches is described in U.S. Pat. No. 5,916,237 to Schu, incorporated herein by reference in its entirety. One issue with inserting a switch in series with a voltage supply is that the voltage drop created by current through the $R_{on}$ impedance of the switch may affect the circuit that is being powered. Because MEMS switches make a direct mechanical connection, their $R_{on}$ impedance is much lower than a typical CMOS switch used for this purpose. The voltage drop across the switch is significantly reduced through the use of MEMS switches. In addition, significant silicon area savings may be realized by integrating MEMS switches to power-down circuits that are not being used.

In FIG. 11, a digital circuit 501 includes a number of MEMS power switches 504, 506, 508 that are controlled by controller 511, which may be a microprocessor or other programmable control device. Many of the elements of circuitry 500 shown in FIG. 11 are intended to represent circuitry typically found in a wide variety of implantable medical devices. Input signals are provided on input signal or bus 516, and output signals are presented on output signal or bus 518. Power provided by power supply 502 is selectively applied to, and removed from, various circuit elements such as logic circuit 510, or registers 512 and 514 of digital circuit 501 in a coordinated manner between controller 511 and MEMS power switches 504, 506, and 508. Control bus 513 contains a group of power control lines 503, 505, and 507, which control the MEMS power switches, as well as a group of enable control lines 509, 515, and 517 which enable and/or disable the logic blocks as part of the power down or power up procedure. In accordance with the present invention, MEMS power switches 504, 506, and 508 are provided as bistable MEMS switches described above.

EXAMPLE

MEMS switches fabricated using the methods described above were evaluated after packaging in a ceramic DIL housing hermetically sealed in nitrogen atmosphere.

Figure 12:
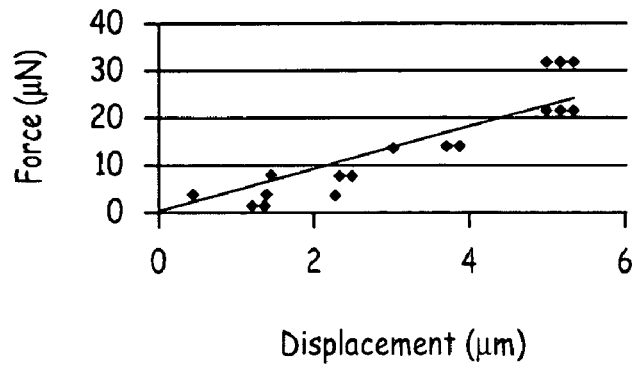
FIG. 12 is plot of the calculated spring force as a function of measured displacement in an operating MEMS switch constructed according to the methods described herein.

FIG. 12 is plot of the calculated spring force as a function of displacement.

Displacement was measured while the force was calculated from the voltage on the actuators. A least squares fit produced a spring constant of 4.6 N/m which was reasonably close to the theoretically predicted value of 4.2 N/m.

Figure 13:
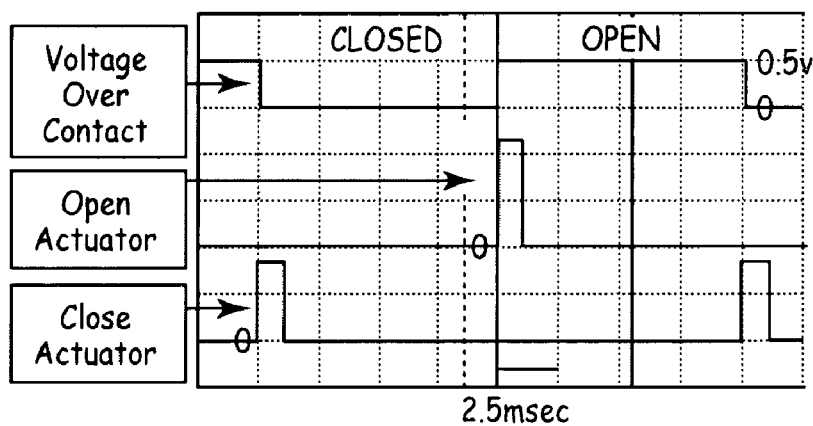
FIG. 13 is a timing diagram of the operation of the bistable MEMS switch of the present invention.

FIG. 13 is a timing diagram of the operation of the bistable MEMS switch of the present invention. The voltage over the contact is approximately 0 when the switch is in a "closed" position. A short voltage pulse is applied to the actuator to cause the switch to change from on "open" to "closed" state. A second pulse applied to the actuator causes the switch to change state from "closed" to "open." The voltage over the contact is approximately 0.5 V in the "open" position. A low contact resistance of less than 10 ohms has been achieved in bistable switch prototypes having a contact force on the order of 10 to 100 µN.

Figure 14:
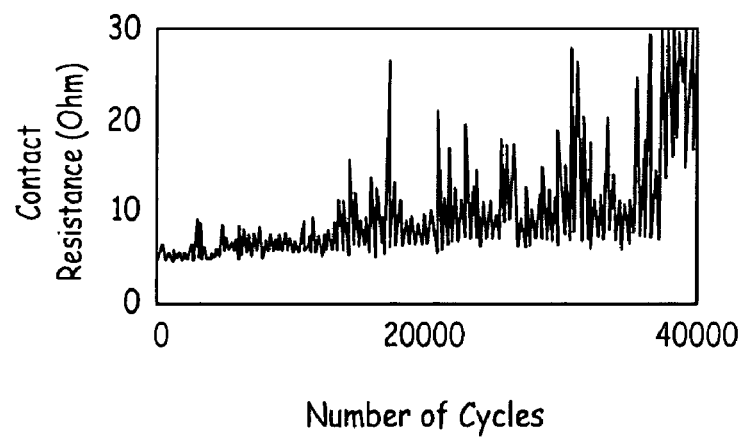
FIG. 14 is a plot of the contact resistance versus the number of state change cycles for a bistable MEMS switch actuated by 18V pulses.

FIG. 14 is a plot of the contact resistance versus the number of state change cycles for a bistable MEMS switch actuated by 18V pulses. Bi-stable switches fabricated according to the methods described herein have shown reliable cycling for over one million cycles. The contact resistance remains below 10 ohms for the first 10,000 cycles and increases substantially after nearly 40,000 cycles. SEM-EDX analysis revealed a loss of gold coverage on contact areas after 40,000 cycles.

In many fields of medicine delivering electrical pulses to the body via a chronically implanted electrode connected to a pulse generator can restore a patient's health. The ability to select electrodes from a plurality of possibilities non-invasively would be advantageous for both the implanting physician and the patient (FIG. 4). Apart from control logic, interconnects and possibly power some form of switching is needed to enable such a feature. The main advantage of bi-stable micro electro mechanical switches over conventional solid state switches is that they present a minimum load on the very tight energy budget of chronically implantable systems. In addition low contact resistance, small size and real isolation could be favorable properties.

Bi-stable switches with out of plane movement of contact members use either a current pulse to change the preferential magnetization of a permalloy cantilever in a permanent external magnetic field or a mechanical latch caused by a thermally actuated two segment multimorph cantilever. Laterally moving bi-stable switches use a compliant structure consisting out of a central slider supported by double pinned arms on both sides or two double pinned arms pushed in two possible directions by a central.

A bi-stable design according to the present invention has a central moving contact member with two stable positions. This is achieved by a dual spring suspension system with hinges and double clamped beams (FIG. 5). According to the present invention, an opposing contact member is touched in the second stable position that closes the electrical contact (FIG. 6). Electrostatic comb actuators can change the switch position. The contact is designed to minimize contact resistance and mechanical wear.

Figure 15:
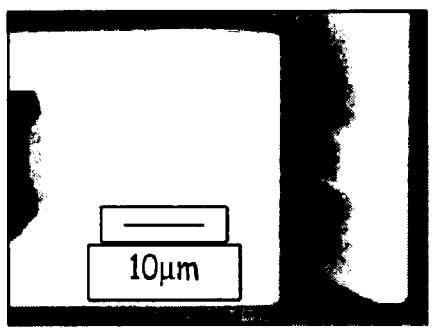
FIG. 15 is a detailed image of contact members according to an embodiment of the present invention.

The switch is fabricated out of a Silicon On Insulator (SOI) wafer (350 um thick carrier layer, 1 um silicon oxide, 80 um device layer, SICO) using a single mask step (FIG. 7). This wafer is dehydrated, treated to enhance adhesion and a 2.3 um resist layer (AZ1518) is spun on and prebaked. The mask pattern (Cr on glass) is transferred to the wafer using a mask aligner (Electronic Visions). The device layer is Deep Reactive Ion Etched (DRIE, Surface Technology Systems). Settings are carefully chosen to prevent notching and create slightly overhanging structures restricting the contact area to the upper side of the device layer where maximum metal coverage is expected. Structures are released in 50% HF and dried with a sublimation technique. As contact material, an annealed Ni/Au alloy was utilized, for example, for minimum contact resistance and sticking. The contact material was evaporated in a special setup, also covering the vertical sidewalls of the silicon structure. The complete wafer is dipped in photo resist before dicing to protect the released structures and individual dies are stripped afterwards. FIG. 8 shows a SEM picture of the completed switch and FIG. 15 is a detailed image of the contact members. As illustrated in FIG. 15, the left portion of the micro contact moves to the right to close the contact.

Design

Figure 16:
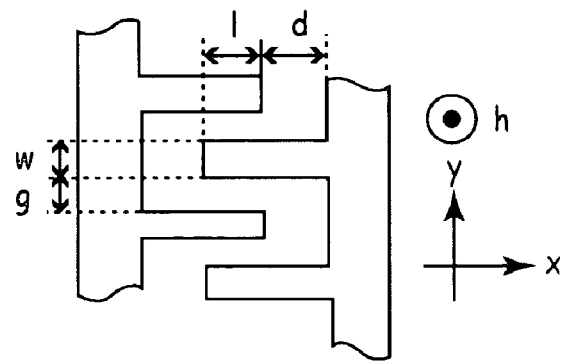
FIG. 16 is a top view of finger members of a bi-stable switch according to an embodiment of the present invention.
Figure 17:
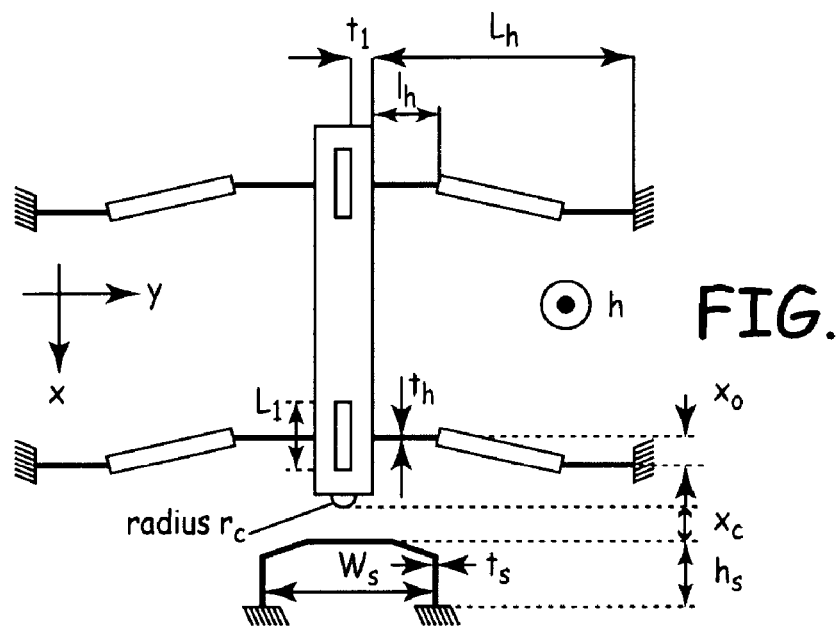
FIG. 17 is a schematic diagram of a mechanical spring system according to an embodiment of the present invention in an initial position.

Structures are designed using the Expert system. The electrostatic comb actuators are shown in FIG. 16 and the mechanical spring system is shown in FIG. 17. FIGS. 16 and 17 define parameters that will be used in the theory to quantitatively describe switch behavior. Typical values are given in Table 1 of FIG. 18. As illustrated in FIG. 16, w is the width of the fingers, g is the gap between the fingers, I is the overlap of the fingers, d is the tip to comb base distance and h is the height of the structure (I and d as fabricated). As illustrated in FIG. 17, when the mechanical spring system is in an initial position, t1 is the thickness and I1 is the length of the double clamped beam, and th is the thickness, Ih is the length and Lh is the arm length of the hinges. In addition, xo is the offset and xc is the contact position, while ts is the thickness, ws is the width and hs the length of the contact spring. The moving contact member contains a bump with radius rc and the complete structure has a height h.

In mono-stable test structures the movable beam is held by a linear spring to better be able to study contact properties. To investigate the influence of the contact shape, asymmetric and dual contact designs are included.

Experimental Setup

Bare die are contacted using an Alessi Industries needle prober with microscope (Mitutuyo) positioned in a class 10000 controlled environment. Standard power supplies are used in combination with EMCO High Voltage amplifiers to create actuation voltage and standard multimeter to measure contact voltage.

Switches were wire bonded in ceramic packages (Kyocera, 8 lead side brazed package) and hermetically sealed in an $N_2$ environment to allow operation outside the cleanroom and easy interconnects in a controlled atmosphere. On some packages glass lids were glued non-hermetically to allow for visual inspection.

Switch dynamics was investigated by providing periodic pulses of controlled duration and magnitude to the actuators while monitoring contact voltage on an oscilloscope (Tektronix TDS3014B). The voltage on the actuator was switched on and off using FET switches (BSS100) with the gate being controlled by a programmable one shot (Tektronix) triggered by a function generator (Yokogawa FG120). For duration testing a data acquisition card was used with both digital and analog I/O capability (NI 6024E) to control the voltage on the actuators and record the contact voltage using a computer with Labview.

Contact resistance as a function of actuator voltage and contact current was measured under computer control (Labview) using the monostable test structures. The voltage on the actuators could be increased in small steps using a programmable high voltage source (Agilent 6030A, via GPIB). The current through the contact was also controlled via GPIB while the voltages were recorded as described above.

Electrostatic Actuators

By modeling the comb fingers (FIG. 16) as parallel plate capacitors, the capacitance C between the two parts of the actuator as a function of displacement x is given by $$C = 2N\varepsilon\left(\frac{wh}{d-x} + \frac{(l+x)h}{g}\right) \quad \text{(Capacitance)}$$

with N the number of moving comb fingers and $\epsilon$ the permittivity of the medium between the combs. The first term is the tip to base contribution ($C_t$) and the second term is the side to side contribution ($C_s$).

The x-derivative of the energy stored in the capacitor when a voltage V is applied over it gives an expression for the attractive force $F_x$ between the two parts of the actuator in x direction $$F_x = N\varepsilon V^2\left(\frac{wh}{(d-x)^2} + \frac{h}{g}\right). \quad \text{(e - Force)}$$

Mechanical System

Total force exerted by the hinges and double clamped beams on the central movable beam (FIG. 17) as a function of displacement is given by $$F_{springs} = -k_h x + \frac{x - x_o}{L_h} k_l \left( \sqrt{x_o^2 + L_h^2} - \sqrt{(x_o - x)^2 + L_h^2} \right) \quad \text{s-Force}$$

with $k_h$, $k_l$ respectively the spring constant of the four hinges and the four double clamped beams given by $$k_h = 2 \frac{Eht_h^3}{4l_h^3 - 6l_h^2 L_h + 3l_h L_h^2} \quad \text{(Hinge)}$$

$$k_l = 4 \frac{16 E h t_l^3}{L_l^3} \quad \text{(Beam)}$$

with E the Youngs modulus of the material. The second term in (s-Force) is a reaction force in x direction due to compression of the double clamped beam in y direction responsible for the bi-stable behavior as shown schematically in FIG. 6.

The force required to close the switch is given by the local minimum in the force-displacement curve. The required force to open it is given by the contact force. Any sticking force will add to this. An upper limit on the parasitic non-electric force the switch can sustain and avoid unintended switching to the alternative state can be found by taking Newton's law of inertia of mass F=ma with a the acceleration, F equal to the minimal required switching force and m the mass of the movable part given by m=Ahp with A the total area of the moving parts and p the density of the material. The mass of the gold layer on top of the silicon should also be taken into account.

For the monostable test structures the spring force $F_{mono}$ is described by $$F_{mono} = -k_m x \quad \text{(F-mono)}$$

$$k_m = \frac{12EI}{l^3} \quad \text{(k-mono)}$$

$$I = \frac{hb^3}{12} \quad \text{(moment of inertia)}$$

with $k_m$ the spring constant, l the moment of inertia and l,h and b the length, height and width of the beam respectively.

Dynamics

Newton's law of inertia gives the differential equation for the displacement as a function of time (dynamics).

$$m \frac{d^2 x}{dt^2} = F_x(V, t) - c \frac{dx}{dt} + F_s(x) + F_{cs}(x) \quad \text{(dynamics)}$$

with m the mass of the structure and c a friction coefficient given by $$c = \mu \frac{A_c}{d_c} \quad \text{(damping)}$$

in which $\mu$ is the absolute viscosity of the medium between the combs, $A_c$ is the total sliding surface area and $d_c$ is the gap between the sliding surfaces.

Resonance for the mono-stable structures is expected at $$\omega_0 = \sqrt{\frac{k}{m}} \quad \text{(resonance)}$$

The energy E needed to change the state of the switch equals the energy stored in the charged actuator given by $$E = \frac{1}{2} C V^2 \quad \text{(switch energy)}$$

with C the capacitance of the actuators and V the switching voltage.

Micro Contact

The contact resistance $R_c$ depends on the contact force $F_c$ as $$R_c \propto F_c^{-\frac{1}{\alpha}} \quad \text{(resistance-force)}$$

with $\alpha=3$ for elastic deformations and $\alpha=2$ for plastic deformations.

Since the hinges are long and thin, they significantly contribute to the measured contact resistance. The measured resistance values are corrected with a value $R_{cor}$ given by $$R_{cor} = \frac{\rho l}{hw} = \rho_s n_s$$

with $\rho_s = \rho/h$ the resistance per square of the gold layer and $n_s = l/w$ the number of squares.

Under adiabatic conditions and using the Wiedemann-Franz law a relation between the voltage over the contact $U_c$ and the contact temperature $T_c$ independent of material properties or contact shape can be found $$T_c = \sqrt{T_0^2 + \frac{U_c^2}{4L_0}} \quad \text{(contact-temp-volt)}.$$

With T0 the ambient temperature and $L_0 = 2.4 \times 10^{-8} V^2 K^{-2}$ (Lorentz number). This contact voltage $U_c$ is not to be confused with the contact voltage $V_c$ on the electrostatic actuators needed to make contact. When the contact temperature reaches the melting temperature of the contact metal the switch will be damaged. Equation (contact-temp-volt) can be used to calculate the corresponding voltage $U_c$ over the contact. This in turn can be related to the maximum current when the contact resistance is known.

First mono-stable test structures were used to verify basic properties of the fabricated structures. Displacement was measured as a function of voltage on the actuators. The electrostatic force is calculated from the voltage over the actuators using equation (e-Force). In equilibrium the spring force $F_{mono}$ equals the electrostatic force $F_x$ $$F_{mono} = F_x \quad \text{(equilibrium)}$$

Figure 19:
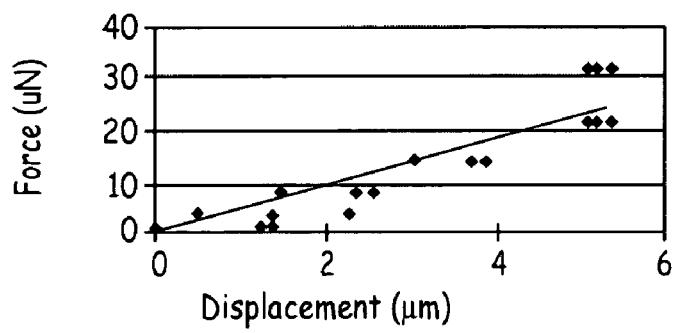
FIG. 19 is a graphical representation of spring force as a function of displacement.

Using this equation the spring force versus displacement can be plotted (FIG. 19). The force is calculated from the voltage on the actuators while the displacement is measured. Fitted value is 4.6N/m for the spring constant, while theoretical expectation was 4.2N/m.

The capacitance was calculated as a function of displacement using a finite element analysis method (Maxwell) and compared with theory (see FIG. 20). The relative capacitance change as a function of voltage was measured and an iterative approach was utilized in which the electrostatic force and spring force are first calculated as a function of displacement for a specific voltage (either using equation e-force or using the derivative of the simulated capacitance). Then equation (equilibrium) is used to find a value for the displacement. Calculation of the capacitance at this displacement yields one point of capacitance and voltage. When the desired range of voltages is calculated the capacitance values are changed to relative units (see FIG. 21). In FIG. 20 the calculated (C) and simulated (Csim) capacitance in fF (vertical axis) are shown as a function of displacement x in μm (horizontal axis) for one comb finger. Ct and Cs represent the contributions from tip to base and side to side respectively. The vertical lines denote the range in which the comb fingers are operated. Note that apart from a constant offset our model applies within this range. FIG. 21 illustrates the relative capacitance change as a function of voltage V (Volt) as measured, calculated and simulated.

Resonance frequency of mono-stable structures was visually determined under the microscope with an AC voltage on the actuators and found at 3.6±0.1 kHz. The calculated resonance using the theoretical value for the spring constant and taking into account the mass off the gold layer on the movable structure is 3.4 kHz.

50V was found as a theoretical value for the contact voltage $V_c$ by using equation (equilibrium) at the contact displacement $x_c$. Experimentally $V_c$ was defined as the first voltage at which the measured contact resistance $R_c$ drops below 10Ω while slowly increasing the voltage on the actuators and find 54V. All measured values were within 10% of expectation.

The bi-stable relay has a contact resistance below 10 Ohm and only 18V are used to change the switch state. The energy needed to change the state of the switch is only 0.2 nJ using an approximate value of 1 pF for the capacitance of the actuators. The dynamic behavior of the relay is shown in FIG. 22, which illustrates voltage over the contact and on the actuators as a function of time during operation of the bi-stable switch. From these measurements the actuator charging time was estimated at 80 μsec, which means an approximate current drain during switching of 200 nA. Sticking of the Ni—Au contact members occurs, indicated by the higher voltage needed to open the switch compared to the closing voltage (24 V vs. 17 V). In the bi-stable design the comb actuators overcome this sticking force. The structures show under damped response. Bouncing could be observed when closing the contact (FIG. 22A). As illustrated in FIGS. 22 and 22A, contact voltage is zero in the closed position and 0.5 V in the open position. A short pulse on the appropriate actuator causes the switch to change state. Bi-stability is shown by the fact that the switch holds its position after removal of the actuator voltage. The detail shows that the switch bounces when closing.

Life cycle testing shows that the bi-stable switches reliably open and close for over $10^6$ times. However, the contact resistance starts increasing after approximately $4.10^4$ times (FIG. 23). SEM-EDX analysis shows damage in gold coverage at the contact spots compared to untouched areas (FIG. 24)

In further investigations contact resistance was measured as a function of contact force and contact current using special mono-stable test structures. Characterization of the contact resistance as a function of contact force is shown in FIG. 26.

DC breakdown of the central moving beam to the opposing fixed contact member with open contact gap (8 μm) was found to be 305V for switches sealed in an $N_2$ environment. Breakdown from the actuators to the carrier layer occurred at 150V.

Figure 25:
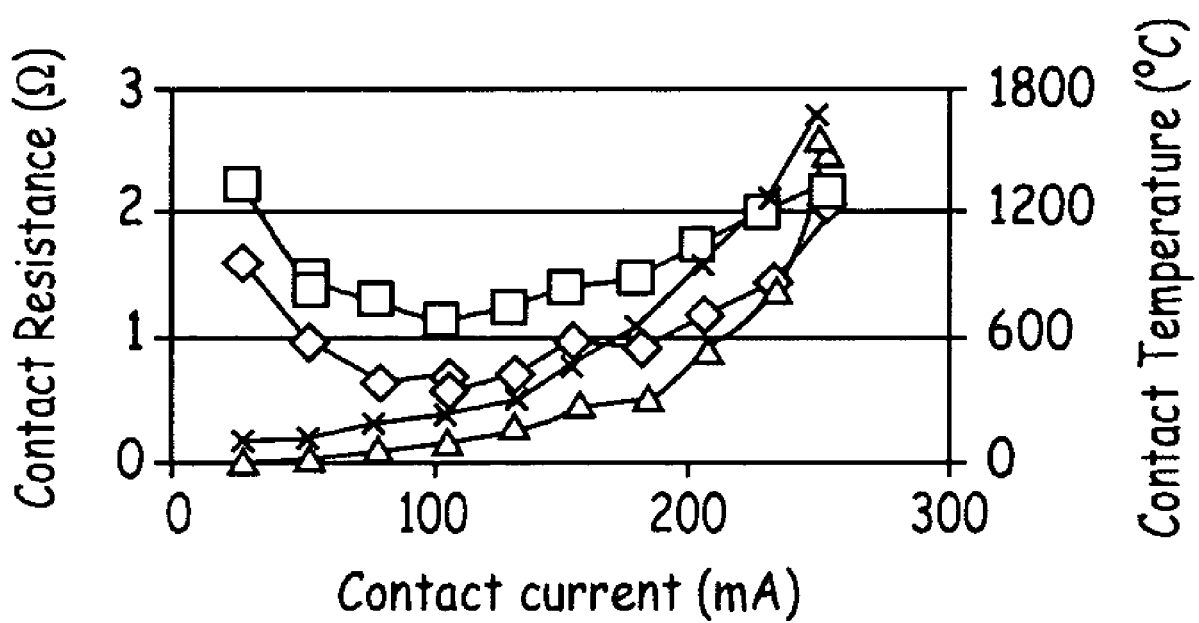
FIG. 25 is a graphical representation of contact-resistance and temperature as a function of contact current.

The critical voltage Uc over the contact is 0.4V. The maximum current was measured through a closed mono-stable contact actuated at 100V corresponding to a contact force of 64 μN and a contact resistance of 3.2-5Ω. The expected maximum current is 258 mA versus a measured value of 257 mA (see FIG. 25).

Although the foregoing description utilizes a cardiac pacing system and associated circuitry for exemplary purposes, the present invention may be employed by any type of IMD, including, but not limited to, defibrillators, cardioverters, neurostimulators, and the like. While the present invention has been illustrated and discussed in terms of the above-described embodiments, it should be understood that the scope of the invention is not to be limited to these exemplary embodiments. Rather, variations of the particular embodiments described herein will occur to those of ordinary skill in the art and yet be within the scope of the invention.

What is claimed is:

1. A MEMS switch comprising:
   a movable beam;
   means for supporting said movable beam;
   actuating means for displacing said movable beam; and
   contact means for interfering said movable beam based on the state of said switch, wherein an Si substrate layer forms an actuation layer, and an Si top layer forms a signal layer.

2. The switch of claim 1 wherein said movable beam is disposed substantially centrally and includes a movable contact.

3. The switch of claim 2 wherein said movable beam includes a suspension system.

4. The switch of claim 1 wherein said actuation means includes an actuator for displacing said movable beam on application of activation signal.

5. The switch of claim 1 wherein said contact means includes a fixed structure.

6. The switch of claim 1 including an actuation layer.

7. The switch of claim 1 including a Si, $SiO_2$ and Si wafer.

8. The switch of claim 1 wherein said actuation layer and said signal layer are electrically decoupled and mechanically coupled by an intervening $SiO_2$ layer.

* * * * *